United States Patent
Furudate et al.

(10) Patent No.: US 11,590,479 B2
(45) Date of Patent: *Feb. 28, 2023

(54) INTERIOR MATERIAL HAVING SURFACE LAYER HAVING VISIBLE LIGHT-RESPONSIVE PHOTOCATALYTIC ACTIVITY, AND METHOD FOR MANUFACTURING SAME

(71) Applicant: SHIN-ETSU CHEMICAL CO., LTD., Tokyo (JP)

(72) Inventors: Manabu Furudate, Kamisu (JP); Tomohiro Inoue, Kamisu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 106 days.

This patent is subject to a terminal disclaimer.

(21) Appl. No.: 16/304,905

(22) PCT Filed: Jun. 22, 2017

(86) PCT No.: PCT/JP2017/022983

§ 371 (c)(1),
(2) Date: Nov. 27, 2018

(87) PCT Pub. No.: WO2018/012240

PCT Pub. Date: Jan. 18, 2018

(65) Prior Publication Data

US 2020/0230575 A1    Jul. 23, 2020

(30) Foreign Application Priority Data

Jul. 14, 2016   (JP) .............................. JP2016-139480

(51) Int. Cl.
| | | |
|---|---|---|
| *B01J 23/28* | (2006.01) | |
| *A61L 2/08* | (2006.01) | |
| *A61L 2/232* | (2006.01) | |
| *B01D 53/86* | (2006.01) | |
| *B01J 21/08* | (2006.01) | |

(Continued)

(52) U.S. Cl.
CPC .............. *B01J 23/28* (2013.01); *A61L 2/084* (2013.01); *A61L 2/088* (2013.01); *A61L 2/232* (2013.01); *B01D 53/8668* (2013.01); *B01J 21/08* (2013.01); *B01J 23/002* (2013.01); *B01J 23/22* (2013.01); *B01J 23/745* (2013.01); *B01J 35/004* (2013.01); *B01J 35/0006* (2013.01); *B01J 37/0009* (2013.01); *B01J 37/0215* (2013.01); *A61L 2202/25* (2013.01); *B01D 2255/2094* (2013.01); *B01D 2255/20707* (2013.01); *B01D 2255/20723* (2013.01);

(Continued)

(58) Field of Classification Search
CPC . B01J 23/28; B01J 21/08; B01J 23/002; B01J 23/22; B01J 23/745; B01J 35/0006; B01J 35/004; B01J 37/0009; B01J 37/0215; A61L 2/084; A61L 2/088; A61L 2/232; B01D 53/8668

See application file for complete search history.

(56) References Cited

U.S. PATENT DOCUMENTS

| | | |
|---|---|---|
| 5,759,948 A | 6/1998 | Akaoka et al. |
| 2011/0198210 A1* | 8/2011 | Hashimoto ............. A61L 9/205 502/345 |

(Continued)

FOREIGN PATENT DOCUMENTS

| | | |
|---|---|---|
| CN | 104640630 A | 5/2015 |
| EP | 1 300 374 A1 | 4/2003 |

(Continued)

OTHER PUBLICATIONS

Sun et al ("Photocatalytic degradation of gaseous o-xylene over M—TiO2 (M=Ag, Fe, Cu, Co) in different humidity levels under visible-light irradiation: activity and kinetic study", Rare Metals, vol. 30, (2011), p. 147-152). (Year: 2011).*

(Continued)

*Primary Examiner* — Colin W. Slifka
*Assistant Examiner* — Michael Forrest
(74) *Attorney, Agent, or Firm* — Birch, Stewart, Kolasch & Birch, LLP

(57) ABSTRACT

The present invention provides: an interior material having a surface layer which has visible light-responsive photocatalytic activity and which contains two types of titanium oxide microparticles, the two types of titanium oxide microparticles comprising first titanium oxide microparticles, in which a tin component and a transition metal component for enhancing visible light responsiveness (excluding iron group components) are in solid solution, and second titanium oxide microparticles, in which an iron group component is in solid solution; and a method for manufacturing the interior material. The present invention makes it possible to provide an interior material in which visible light-responsive photocatalytic titanium oxide microparticles, which make it possible to easily produce a surface layer (photocatalyst thin film) having high transparency and expressing photocatalytic activity even in response to visible light (400-800 nm) only, are applied onto a surface, whereby it is possible to obtain, under indoor illumination, excellent photocatalytic properties such as an antimicrobial property and a property of breaking down chemical substances in indoor air without adversely affecting the design quality of the article in question.

22 Claims, No Drawings

(51) Int. Cl.

| | |
|---|---|
| *B01J 23/00* | (2006.01) |
| *B01J 23/22* | (2006.01) |
| *B01J 23/745* | (2006.01) |
| *B01J 35/00* | (2006.01) |
| *B01J 37/00* | (2006.01) |
| *B01J 37/02* | (2006.01) |
| *E04F 13/08* | (2006.01) |

(52) U.S. Cl.
 CPC .............. *B01D 2255/20769* (2013.01); *B01D 2255/802* (2013.01); *B01D 2257/708* (2013.01); *E04F 13/08* (2013.01)

(56) References Cited

U.S. PATENT DOCUMENTS

| | | | |
|---|---|---|---|
| 2012/0214667 A1 | 8/2012 | Furudate et al. | |
| 2014/0011674 A1* | 1/2014 | Tsai | B01J 35/002 502/330 |
| 2014/0178694 A1* | 6/2014 | Reenberg | B05D 3/007 427/407.1 |
| 2014/0309103 A1 | 10/2014 | Furudate et al. | |
| 2015/0273440 A1* | 10/2015 | Furudate | B01J 21/063 502/242 |
| 2016/0001266 A1 | 1/2016 | Kojima et al. | |
| 2018/0117567 A1 | 5/2018 | Furudate et al. | |

FOREIGN PATENT DOCUMENTS

| | | |
|---|---|---|
| EP | 3 275 536 A1 | 1/2018 |
| JP | 7-303835 A | 11/1995 |
| JP | 2003-334453 A | 11/2003 |
| JP | 2009-148700 A | 7/2009 |
| JP | 2010-104913 A | 5/2010 |
| JP | 2011-136879 A | 7/2011 |
| JP | 2012-210632 A | 11/2012 |
| JP | 2013-126654 A | 6/2013 |
| JP | 2013-198890 A | 10/2013 |
| JP | WO2014/045861 A1 | 3/2014 |
| TW | 201442780 A | 11/2014 |
| WO | WO 2011/145385 A1 | 11/2011 |
| WO | WO 2014/045861 A1 | 3/2014 |
| WO | WO 2016/152487 A1 | 9/2016 |

OTHER PUBLICATIONS

Extended European Search Report dated Feb. 5, 2020, in European Patent Appiication No. 17827370.2.
International Search Report, issued in PCT/JP2017/022983, dated Sep. 5, 2017.
Written Opinion of the International Searching Authority, issued in PCT/JP2017/022983, dated Sep. 5, 2017.
Taiwanese Office Action and Search Report for Taiwanese Application No. 106123373, dated Mar. 3, 2021.

* cited by examiner

INTERIOR MATERIAL HAVING SURFACE LAYER HAVING VISIBLE LIGHT-RESPONSIVE PHOTOCATALYTIC ACTIVITY, AND METHOD FOR MANUFACTURING SAME

TECHNICAL FIELD

The present invention relates to an interior material having on a surface thereof a photocatalytic layer which has a visible light-responsive photocatalytic activity. More particularly, the invention relates to an interior material which has a surface layer that is highly transparent and possesses a visible light-responsive photocatalytic activity, which material manifests a photocatalytic activity even under exposure only to visible light (400 to 800 nm), and to a method for producing the same.

BACKGROUND ART

Photocatalytic titanium oxide fine particles are frequently used in such applications as the cleaning, deodorization and disinfection of substrate surfaces. In this specification, the term "photocatalytic reaction" refers to a reaction caused by excited electrons and holes generated due to the absorption of light by titanium oxide. The decomposition of organic matter is thought to arise primarily by mechanisms such as the following: (1) the excited electrons and holes that have formed carry out oxidation-reduction reactions with oxygen and water adsorbed to the titanium oxide surface, generating active species which decompose organic matter; and (2) the holes that have formed directly oxidize and decompose organic matter adsorbed to the titanium oxide surface.

Studies have been carried out recently which attempt to apply such photocatalysis not only to outdoor uses where ultraviolet light can be utilized, but also to indoor spaces illuminated with light sources such as fluorescent lamps that emit primarily visible-spectrum light (wavelength, 400 to 800 nm). For example, a tungsten oxide photocatalytic body has been disclosed as a visible light-responsive photocatalyst (JP-A 2009-148700; Patent Document 1), but because tungsten is a scarce element, there exists a desire for improvements in the visible light activity of photocatalysts that utilize the widely available element titanium.

Methods for increasing the visible light activity of photocatalysts which use titanium oxide include methods that entail supporting iron or copper on the surface of titanium oxide fine particles or metal-doped titanium oxide fine particles (see, for example, JP-A 2012-210632: Patent Document 2; and JP-A 2010-104913: Patent Document 3), and a method which separately prepares titanium oxide fine particles containing in solid solution (i.e., doped with) tin and a transition metal that increases the visible light activity and titanium oxide fine particles containing in solid solution copper and then uses these separately prepared particles in admixture (WO 2014/045861: Patent Document 4).

The latter of these methods (Patent Document 4), that is, the method which separately prepares titanium oxide fine particles containing in solid solution tin and a transition metal that increases the visible light activity and titanium oxide fine particles containing in solid solution copper and then uses these separately prepared particles in admixture, has the advantage that because the metals other than titanium that are used are all contained in solid solution within the titanium oxide fine particles, the particles are stable and do not readily deteriorate, enabling a photocatalytic thin film of high durability to be obtained. However, a method that further increases the visible-light activity of the photocatalyst is desired.

PRIOR ART DOCUMENTS

Patent Documents

Patent Document 1: JP-A 2009-148700
Patent Document 2: JP-A 2012-210632
Patent Document 3: JP-A 2010-104913
Patent Document 4: WO 2014/045861
Patent Document 5: JP-A H07-303835

SUMMARY OF INVENTION

Technical Problem

In light of the above circumstances, an object of this invention is to provide, by combining and mixing together titanium oxide fine particles containing in solid solution different transition metals, an interior material which has a surface layer that possesses a visible light-responsive photocatalytic activity and which is capable of obtaining a high visible light activity differing from that of the prior art. A further object is to provide a method for producing such an interior material.

Solution to Problem

One approach taken by the inventors to achieve the above objects has been to conduct a search for novel materials that exhibit a high photocatalytic activity only under visible light conditions by using, as the first type of titanium oxide fine particle used in Patent Document 4, titanium oxide fine particles containing in solid solution tin and a transition metal that increases the visible light activity, and by varying the second type of titanium oxide fine particle that is combined therewith. In the course of this investigation, although the titanium oxide fine particles containing a copper constituent in solid solution which are the second type of titanium oxide fine particle used in Patent Document 4 exhibit some photocatalytic activity even under visible light (400 to 800 nm) only conditions, the inventors have found that, surprisingly, when titanium oxide fine particles containing an iron constituent in solid solution—which particles by themselves exhibit substantially no photocatalytic activity under visible light only conditions—are included as the second type of titanium oxide fine particle, a photocatalytic activity equal to or higher than that obtained from combination with titanium oxide fine particles containing a copper constituent in solid solution is exhibited under visible light only conditions.

The inventors have discovered that, by providing a surface layer containing visible light-responsive photocatalytic titanium oxide in which such titanium oxide fine particles containing an iron constituent in solid solution are included as the second type of titanium oxide fine particle, there can be obtained an interior material which exhibits a higher decomposing activity under visible light irradiation than in the prior art, ultimately arriving at the present invention.

By using the interior material of the invention, it is anticipated that harmful substances such as volatile organic compounds (VOCs) which off-gas from construction materials, furnishings, articles of daily use, fabric goods, etc. and contaminate indoor air, becoming a cause of sick-house syndrome, can be decomposed, keeping the indoor air clean.

Accordingly, this invention provides an interior material having a surface layer that has a visible light-responsive photocatalytic activity, and a method for producing the same.

[1]

An interior material which has a surface layer having a visible light-responsive catalytic activity, wherein the surface layer includes two types of titanium oxide fine particles: a first type of titanium oxide fine particle which contains in solid solution a tin constituent and a transition metal constituent (exclusive of iron group constituents) that increases visible light responsiveness, and a second type of titanium oxide fine particle which contains in solid solution an iron group constituent.

[2]

The interior material of [1], wherein the content of the tin constituent included in the first type of titanium oxide fine particle, expressed as a molar ratio with titanium (Ti/Sn), is from 1 to 1,000.

[3]

The interior material of [1] or [2], wherein the transition metal constituent in solid solution within the first type of titanium oxide fine particle is at least one selected from the group consisting of vanadium, chromium, manganese, niobium, molybdenum, rhodium, tungsten and cerium.

[4]

The interior material of [3], wherein the transition metal constituent in solid solution within the first type of titanium oxide fine particle is molybdenum and/or vanadium.

[5]

The interior material of [4], wherein the content of the molybdenum constituent included in the first type of titanium oxide fine particle, expressed as a molar ratio with titanium (Ti/Mo), is from 1 to 1,000 and/or the content of the vanadium constituent, expressed as a molar ratio with titanium (Ti/V), is from 10 to 10,000.

[6]

The interior material of any of [1] to [5], wherein the content of the iron group constituent included in the second type of titanium oxide fine particle, expressed as a molar ratio with titanium (Ti/iron group constituent), is from 1 to 1,000.

[7]

The interior material of any of [1] to [6], wherein the iron group constituent in solid solution within the second type of titanium oxide fine particle is an iron constituent.

[8]

The interior material of any of [1] to [7], wherein the first type of titanium oxide fine particle and the second type of titanium oxide fine particle have a mixing ratio therebetween, expressed as the weight ratio [(first type of titanium oxide fine particle)/(second type of titanium oxide fine particle)], of from 99 to 0.01.

[9]

The interior material of any of [1] to [8], wherein the surface layer further contains a binder.

[10]

The interior material of [9], wherein the binder is a silicon compound-based binder.

[11]

The interior material of any of [1] to [10] which is a member selected from the group consisting of indoor construction materials, interior materials within a vehicle, furnishings and electrical appliances.

[12]

A method for producing an interior material, which method includes the step of forming a surface layer having a visible light-responsive catalytic activity by applying, to the surface of an interior material body, a dispersion in which are dispersed two types of titanium oxide fine particles: a first type of titanium oxide fine particle which contains in solid solution a tin constituent and a transition metal constituent (exclusive of iron group constituents) that increases visible light responsiveness, and a second type of titanium oxide fine particle which contains in solid solution an iron group constituent.

[13]

The method for producing an interior material of [12], wherein the method of applying the dispersion is spray coating, flow coating, dip coating, spin coating, Meyer bar coating, gravure coating, knife coating, kiss coating, die coating or film transfer.

Advantageous Effects of Invention

An advantageous effect of this invention is that, by applying to a surface visible light-responsive photocatalytic titanium oxide fine particles from which a photocatalytic thin film (surface layer) that is of high transparency and manifests a photocatalytic activity even when exposed only to visible light (400 to 800 nm) can easily be produced, an interior material can be provided which, under indoor lighting, is able to achieve excellent photocatalytic performances, such as an indoor air chemical substance-decomposing performance and a disinfecting performance, without a loss in the decorativeness of the article.

DESCRIPTION OF EMBODIMENTS

The invention is described more fully below.

The interior material of the invention has an interior material body and a surface layer formed on a surface of the body. The surface layer has a visible light-responsive photocatalytic activity. The method of forming this surface layer having a visible light-responsive photocatalytic activity is not particularly limited. For example, the surface layer may be formed by using the subsequently described coating method or the like to apply a visible light-responsive photocatalytic titanium oxide fine-particle dispersion onto the surface of the interior material body and then drying the applied dispersion.

The visible light-responsive photocatalytic titanium oxide fine-particle dispersion is described in detail below.

<Visible Light-Responsive Photocatalytic Titanium Oxide Fine-Particle Dispersion>

The visible light-responsive photocatalytic titanium oxide fine-particle dispersion is made up of titanium oxide fine particles of differing compositions—referred to herein as a "first type" of titanium oxide fine particle and a "second type" of titanium oxide fine particle—that are dispersed in an aqueous dispersion medium. Titanium oxide fine particles of the first type are titanium oxide fine particles containing in solid solution a tin constituent and a transition metal constituent (exclusive of iron group constituents); titanium oxide fine particles of the second type are titanium oxide fine particles containing in solid solution an iron group constituent.

As used herein, "solid solution" refers to a phase in which atoms at lattice points in one given crystal phase are substituted with other atoms or in which other atoms have entered into lattice interstices; that is, it refers to a mixed phase which can be thought of as a given crystal phase having another substance dissolved therein, the crystal phase being understood here to be a homogeneous phase. A solid solution in which solvent atoms at lattice points are substituted with solute atoms is called a "substituted solid solution," and a solid solution in which solute atoms have entered into lattice interstices is called an "interstitial solid solution." Here, "solid solution" may refer to either of these.

The titanium oxide fine particles are characterized by, in the first type of titanium oxide fine particle, the formation of a solid solution of titanium oxide, tin and a transition metal atom (exclusive of iron group constituents) and, in the second type of titanium oxide fine particle, the formation of a solid solution of titanium oxide and an iron group constituent. The solid solution may be either a substituted solid solution or an interstitial solid solution. A substituted solid solution is one that forms with the substitution of various metal atoms at titanium sites in the titanium oxide crystals, and an interstitial solid solution is one that forms with the entry of various metal atoms into lattice interstices in the titanium oxide crystals. When various metal atoms enter into solid solution in titanium oxide, in measurement of the crystal phase by x-ray diffraction analysis or the like, only peaks for the crystal phases of titanium oxide are observed; peaks for compounds attributable to the various metal atoms that have been added are not observed.

Methods of forming solid solutions of different metals in metal oxide crystals include, without particular limitation, vapor phase methods (e.g., chemical vapor deposition, physical vapor deposition), liquid phase methods (e.g., hydrothermal method, sol-gel method), and solid phase methods (e.g., high-temperature firing).

Titanium oxide fine particles are generally known to have three crystal phases: rutile, anatase and brookite. The use of chiefly rutile and anatase in both the first type of titanium oxide fine particle and the second type of titanium oxide fine particle is preferred. In addition, of rutile and anatase, it is preferable for the first type of titanium oxide fine particle to be chiefly rutile and it is preferable for the second type of titanium oxide fine particle to be chiefly anatase. "Chiefly" here means generally at least 50 wt %, preferably at least 70 wt %, and more preferably at least 90 wt %, and may even be 100 wt %, of all the titanium oxide fine-particle crystals.

The dispersion medium used in the dispersion is typically an aqueous solvent, with the use of water being preferred, although a mixed solvent of water and a hydrophilic organic solvent that mixes with water in any ratio may be used. The water is preferably, for example, deionized water, distilled water, or purified water. The hydrophilic organic solvent is preferably, for example, an alcohol such as methanol, ethanol or isopropanol; a glycol such as ethylene glycol; or a glycol ether such as ethylene glycol monomethyl ether, ethylene glycol monoethyl ether or propylene glycol n-propyl ether. When a mixed solvent is used, the ratio of hydrophilic organic solvent in the mixed solvent is preferably more than 0 and not more than 50 wt %, more preferably not more than 20 wt %, and even more preferably not more than 10 wt %.

The first type of titanium oxide fine particle is a titanium oxide fine particle which contains in solid solution a tin constituent and a transition metal constituent other than iron group constituents that increases the visible light activity. Transition metals are elements selected from among Groups 3 to 11 of the Periodic Table. The transition metal constituent that increases the visible light activity is preferably selected from among vanadium, chromium, manganese, niobium, molybdenum, rhodium, tungsten and cerium. Of these, the selection of molybdenum and/or vanadium is preferred.

The tin constituent that forms a solid solution in the first type of titanium oxide fine particle is used to increase the visible light responsiveness of the photocatalytic thin film, and may be any tin constituent derived from a tin compound, such as tin metal (Sn), oxides (SnO, $SnO_2$), hydroxides, chlorides ($SnCl_2$, $SnCl_4$), nitrates ($Sn(NO_3)_2$), sulfates ($SnSO_4$), halides and complex compounds. These may be used singly or two or more may be used in combination. Of these, the use of oxides (SnO, $SnO_2$), chlorides ($SnCl_2$, $SnCl_4$) or sulfates ($SnSO_4$) is preferred.

The content of tin constituent in the first type of titanium oxide fine particle, expressed as a molar ratio with titanium (Ti/Sn), is from 1 to 1,000, preferably from 2 to 500, and more preferably from 5 to 100. When the molar ratio is less than 1, the titanium oxide content decreases and a sufficient photocatalytic effect may not be exhibited. When the molar ratio is greater than 1,000, the visible light responsiveness may be inadequate.

The transition metal constituent contained in solid solution within the first type of titanium oxide fine particle may be any derived from compounds of the transition metal, such as the metal, oxides, hydroxides, chlorides, nitrates, sulfates, halides and various complex compounds. These may be used singly or two or more may be used together.

The content of the transition metal constituent in the first type of titanium oxide fine particle may be suitably selected according to the type of transition metal constituent. However, expressed as the molar ratio with titanium (Ti/transition metal), the content is preferably in the range of 1 to 10,000, and especially the range of 5 to 1,000.

Here, when molybdenum is selected as the transition metal constituent to be included in solid solution within the first type of titanium oxide fine particle, the molybdenum constituent may be any that is derived from molybdenum compounds, and is exemplified by molybdenum metal (Mo), oxides ($MoO_2$, $MoO_3$), hydroxides, chlorides ($MoCl_3$, $MoCl_5$), nitrates, sulfates, halides and complex compounds. These may be used singly or two or more may be used in combination. Of these, the use of oxides ($MoO_2$, $MoO_3$) or chlorides ($MoCl_3$, $MoCl_5$) is preferred.

The content of the molybdenum constituent in the first type of titanium oxide fine particle, expressed as the molar ratio with titanium (Ti/Mo), is from 1 to 1,000, preferably from 2 to 100, and more preferably from 2 to 50. The reason for this range is that at a molar ratio below 1, the titanium oxide content becomes low and a sufficient photocatalytic effect may not be exhibited, and at a molar ratio greater than 1,000, the visible light responsiveness may be inadequate and a high decomposition activity at low acetaldehyde concentrations may not be obtained.

When vanadium is selected as the transition metal constituent to be included in solid solution within the first type of titanium oxide fine particle, the vanadium constituent may be any that is derived from vanadium compounds, and is exemplified by vanadium metal (V), oxides (VO, $V_2O_3$, $VO_2$, $V_2O_5$), hydroxides, chlorides ($VCl_5$), the oxychloride ($VOCl_3$), nitrates, sulfates, the oxysulfate ($VOSO_4$), halides and complex compounds. These may be used singly or two or more may be used in combination. Of these, the use of oxides ($V_2O_3$, $V_2O_5$), chlorides ($VCl_5$), the oxychloride ($VOCl_3$) or the oxysulfate ($VOSO_4$) is preferred.

The content of the vanadium constituent in the first type of titanium oxide fine particle, expressed as the molar ratio with titanium (Ti/V), is from 10 to 10,000, preferably from 100 to 10,000, and more preferably from 100 to 5,000. The reason for this range is that at a molar ratio below 10, the titanium oxide crystal content becomes low and a sufficient photocatalytic effect may not be exhibited, and at a molar ratio greater than 10,000, the visible light responsiveness may be inadequate and a high decomposition activity at low acetaldehyde concentrations may not be obtained.

Molybdenum and vanadium may both be selected as the transition metal constituent included in the first type of titanium oxide fine particle. Their respective contents in this case may be selected from the above ranges, provided that the molar ratio between the sum of these contents and titanium, expressed as [Ti/(Mo+V)], is 1 or more but not more than 10,000.

The first type of titanium oxide fine particle may be of one kind used alone, or may be of two or more kinds used in combination. When two or more kinds having differing visible light responsivenesses are combined, a visible light activity-increasing effect may be obtained.

The second type of titanium oxide fine particle has a composition that differs from that of the first type of titanium oxide fine particle and is characterized by containing in solid solution an iron group constituent. The general form is one which, unlike the first type of titanium oxide fine particle, includes no tin and no transition metal other than an iron group constituent.

The iron group metal contained in solid solution within the second type of titanium oxide fine particle is exemplified by iron, cobalt and nickel. Of these, iron is preferred.

The iron group constituent contained in solid solution within the second type of titanium oxide fine particle may be any that is derived from iron group compounds, such as iron metal (Fe), oxides ($Fe_2O_3$, $Fe_3O_4$), hydroxides (FeO(OH)), chlorides ($FeCl_2$, $FeCl_3$), nitrates ($Fe(NO_3)_3$), sulfates ($FeSO_4$, $Fe_2(SO_4)_3$), halides and complex compounds. These may be used singly or two or more may be used in combination. Of these, the use of oxides ($Fe_2O_3$, $Fe_3O_4$), hydroxides (FeO(OH)), chlorides ($FeCl_2$, $FeCl_3$), nitrates ($Fe(NO_3)_3$) and sulfates ($FeSO_4$, $Fe_2(SO_4)_3$) is preferred.

The content of the iron group constituent in the second type of titanium oxide fine particle, expressed as the molar ratio with titanium (Ti/iron group constituent) is from 1 to 1,000, preferably from 2 to 200, and more preferably from 5 to 100. The reason for this range is that at a molar ratio below 1, the titanium oxide content becomes low and a sufficient photocatalytic effect may not be exhibited, and at a molar ratio greater than 1,000, the visible light responsiveness may be inadequate.

The first type of titanium oxide fine particle and second type of titanium oxide fine particle in the visible light-responsive photocatalytic titanium oxide fine-particle dispersion have a volume-based 50% cumulative distribution size ($D_{50}$) measured by dynamic laser light scattering (which size is also referred to below as the "average particle size") of preferably from 5 to 30 nm, and more preferably from 5 to 20 nm. This is because, at an average particle size below 5 nm, the photocatalytic activity may be inadequate, and at more than 30 nm, the dispersion may become opaque. Instruments that may be used to measure the average particle size include, for example, the Nanotrac UPA-EX150 (Nikkiso Co., Ltd.) and the LA-910 (Horiba, Ltd.).

The first type of titanium oxide fine particle and the second type of titanium oxide fine particle included in the visible light-responsive photocatalytic titanium oxide fine-particle dispersion have a mixing ratio therebetween, expressed as the weight ratio [(first type of titanium oxide fine particle)/(second type of titanium oxide fine particle)], of preferably from 99 to 0.01, more preferably from 19 to 0.05, and even more preferably from 9 to 1. This is because, at a weight ratio in excess of 99 or below 0.01, the visible light activity may be inadequate.

From the standpoint of the ease of forming a surface layer (photocatalytic thin film) of the required thickness, the total concentration of the first type of titanium oxide fine particle and the second type of titanium oxide fine particle in the visible light-responsive photocatalytic titanium oxide fine-particle dispersion is preferably from 0.01 to 20 wt %, and especially from 0.5 to 10 wt %.

In addition, a binder may be added to the visible light-responsive photocatalytic titanium oxide fine-particle dispersion, both for the purpose of making the dispersion easier to apply to the surface of the subsequently described various types of members and also to make the fine particles readily adhering. Examples of binders include silicon, aluminum, titanium, zirconium and other metal compound-based binders, and fluoroplastic, acrylic resin, urethane resin and other organic resin-based binders.

The binder is added and used in a weight ratio between the binder and the titanium oxide, expressed as (binder/titanium oxide), of preferably from 0.01 to 99, more preferably from 0.1 to 9, and even more preferably from 0.4 to 2.5. The reason is that, at a weight ratio below 0.01, adherence of the titanium oxide fine particles to the surface of various types of members may be inadequate, and at a weight ratio above 99, the visible light activity may be inadequate.

In particular, to obtain an excellent surface layer (photocatalytic thin film) having a high photocatalysis and transparency, it is especially desirable for a silicon compound-based binder to be added and used in a compounding ratio (weight ratio between silicon compound and titanium oxide) of preferably from 1:99 to 99:1, more preferably from 10:90 to 90:10, and even more preferably from 30:70 to 70:30. Here, "silicon compound-based binder" refers to a colloidal dispersion, solution or emulsion of a silicon compound that is obtained by including a solid or liquid silicon compound in an aqueous dispersion medium. Illustrative examples include colloidal silica (preferred particle size, 1 to 150 nm); solutions of silicates; silane and siloxane hydrolyzate emulsions; silicone resin emulsions; and emulsions of copolymers of a silicone resin with another resin, such as silicone-acrylic resin copolymers and silicone-urethane resin copolymers.

Also, a hydrophilic organic solvent or a surfactant or the like may be added in order to increase the coatability onto an interior material of a liquid coating obtained by addition of the visible light-responsive photocatalytic titanium oxide fine-particle dispersion and a binder.

Preferred hydrophilic organic solvents include alcohols such as methanol, ethanol and isopropanol; glycols such as ethylene glycol; and glycol ethers such as ethylene glycol monomethyl ether, ethylene glycol monoethyl ether and propylene glycol n-propyl ether. In cases where a hydrophilic organic solvent is used, the proportion of hydrophilic organic solvent in the photocatalytic dispersion or liquid coating is greater than 0 wt % and preferably not more than 50 wt %, more preferably not more than 20 wt %, and even more preferably not more than 10 wt %.

Examples of the surfactant include anionic surfactants such as fatty acid sodium salts, alkylbenzenesulfonates, fatty alcohol sulfates and polyoxyethylene alkyl ether sulfates; cationic surfactants such as alkyltrimethylammonium salts, dialkyldimethylammonium salts, alkyldimethylbenzylammonium salts and quaternary ammonium salts; amphoteric surfactants such as alkylamino fatty acid salts, alkyl betaines and alkyl amine oxides; nonionic surfactants such as polyoxyethylene alkyl ethers, polyoxyethylene alkyl phenol ethers, alkyl glycosides, polyoxyethylene fatty acid esters, sucrose fatty acid esters, sorbitan fatty acid esters, polyoxyethylene sorbitan fatty acid esters and fatty acid alkanolamides; and polymer surfactants. Of these, from the standpoint of the stability of the dispersion, a nonionic surfactant is preferred.

In cases where a surfactant is used, the concentration of surfactant with respect to 100 wt % of the overall composition within the photocatalytic dispersion or the liquid coating (i.e., 100 wt % of the total of the above titanium oxide fine particles, binder, solvent and surfactant) is greater than 0 wt %, preferably from 0.001 to 5 wt %, more preferably from 0.01 to 1.0 wt %, and even more preferably from 0.05 to 0.5 wt %.

<Method of Producing Visible Light-Responsive Photocatalytic Titanium Oxide Fine-Particle Dispersion>

The above visible light-responsive photocatalytic titanium oxide fine-particle dispersion is produced by preparing both a dispersion of the first type of titanium oxide fine particle (first titanium oxide fine-particle dispersion) and a dispersion of the second type of titanium oxide fine particle (second titanium oxide fine-particle dispersion), and then mixing together the first titanium oxide fine-particle dispersion and the second titanium oxide fine-particle dispersion.

The production method is exemplified by a method that includes the following Steps (1) to (5):

(1) preparing a tin and transition metal-containing peroxotitanic acid solution from a starting titanium compound, a tin compound, a transition metal compound (exclusive of iron group compounds), a basic substance, hydrogen peroxide and an aqueous dispersion medium;
(2) preparing a tin and transition metal-containing titanium oxide fine-particle dispersion by heating the tin and transition metal-containing peroxotitanic acid solution prepared in Step (1) at from 80 to 250° C. under pressure control;
(3) preparing an iron group element-containing peroxotitanic acid solution from a starting titanium compound, an iron group compound, a basic substance, hydrogen peroxide and an aqueous dispersion medium;
(4) preparing an iron group element-containing titanium oxide fine-particle dispersion by heating the iron group element-containing peroxotitanic acid solution prepared in Step (3) at from 80 to 250° C. under pressure control; and
(5) mixing together the two titanium oxide fine-particle dispersions prepared in Steps (2) and (4).

Steps (1) and (2) are steps for obtaining the first titanium oxide fine-particle dispersion, Steps (3) and (4) are steps for obtaining the second titanium oxide fine-particle dispersion, and Step (5) is a final step for obtaining a dispersion containing both the first type of titanium oxide fine particle and the second type of titanium oxide fine particle.

As already mentioned, because using a molybdenum compound and/or a vanadium compound as the transition metal compounds employed in Step (1) is preferred, each of the steps is described in detail below for cases in which a molybdenum compound and/or a vanadium compound are used.

Step (1):

In Step (1), a transition metal and tin-containing peroxotitanic acid solution is prepared by reacting a starting titanium compound, a transition metal compound, a tin compound, a basic substance and hydrogen peroxide in an aqueous dispersion medium.

The reaction method may be either a method that adds the basic substance to the starting titanium compound within the aqueous dispersion medium to form titanium hydroxide, removes impurity ions other than the metallic ions included, adds hydrogen peroxide to form peroxotitanic acid, and then adds the transition metal compound and the tin compound, thereby giving a transition metal and tin-containing peroxotitanic acid solution; or a method that adds the transition metal compound and the tin compound to the starting titanium compound and the basic substance within an aqueous dispersion medium and effects dissolution so as to form a transition metal and tin-containing titanium hydroxide, removes impurity ions other than the metallic ions included, and subsequently adds hydrogen peroxide, thereby giving a transition metal and tin-containing peroxotitanic acid solution.

Moreover, in the first stage of the latter method, the starting titanium compound and the basic substance within the aqueous dispersion medium may be separated into two aqueous dispersion media (two liquids), such as an aqueous dispersion medium in which the starting titanium compound is dispersed and an aqueous dispersion medium in which the basic substance is dispersed, and the transition metal compound and the tin compound may be dissolved in one or both of these two liquids, depending on the solubilities of these respective compounds in the two liquids, after which both solutions may be mixed together.

After a transition metal and tin-containing peroxotitanic acid solution is thus obtained, the solution is furnished to the hydrothermal reaction in subsequently described Step (2), thereby enabling titanium oxide fine particles in which these respective metals are present in solid solution with titanium oxide to be obtained.

Examples of the starting titanium compound include inorganic acid salts of titanium, such as chlorides, nitrates, and sulfates; organic acid salts such as the titanium salts of formic acid, citric acid, oxalic acid, lactic acid and glycolic acid; and the titanium hydroxide that settles out when hydrolysis is carried out by adding an alkali to aqueous solutions of these. Such starting titanium compounds may be used singly or two or more may be used in combination. Of these, the use of titanium chlorides ($TiCl_3$, $TiCl_4$) is preferred.

The transition metal compound, the tin compound and the aqueous dispersion medium, each of which has been described above, are used by being compounded in the foregoing manner. The concentration of the starting titanium compound aqueous solution formed of the starting titanium compound and the aqueous dispersion medium is preferably 60 wt % or less, and more preferably 30 wt % or less. The concentration lower limit is set as appropriate, although a concentration of at least 1 wt % is generally preferred.

The purpose of the basic substance is to smoothly convert the starting titanium compound into titanium hydroxide. Illustrative examples include hydroxides of alkali metals or alkaline earth metals, such as sodium hydroxide and potassium hydroxide; and amine compounds such as ammonia, alkanolamines and alkylamines. The basic substance is added and used in an amount such as to bring the pH of the aqueous solution of the starting titanium compound to 7 or above, and especially from 7 to 10. The basic substance may be used together with the aqueous dispersion medium after first being rendered into an aqueous solution of a suitable concentration.

The purpose of the hydrogen peroxide is to convert the starting titanium compound or titanium hydroxide into peroxotitanium—that is, a titanium oxide compound containing a Ti—O—O—Ti bond, and is typically used in the form of hydrogen peroxide water. The amount of hydrogen peroxide added is preferably set to from 1.5 to 20 moles per mole of transition metal, titanium and tin combined. When adding hydrogen peroxide and converting the starting titanium compound or titanium hydroxide into peroxotitanic acid, the reaction temperature is preferably set to from 5 to 80° C. and the reaction time is preferably set to from 30 minutes to 24 hours.

The resulting transition metal and tin-containing peroxotitanic acid solution may, for the sake of pH adjustment, etc., include an alkaline substance or an acidic substance. Illustrative examples of what is referred to here as the alkaline substance include ammonia, sodium hydroxide and calcium hydroxide. Illustrative examples of the acidic substance include inorganic acids such as sulfuric acid, nitric acid, hydrochloric acid, carbonic acid, phosphoric acid and hydrogen peroxide; and organic acids such as formic acid, citric acid, oxalic acid, lactic acid and glycolic acid. The pH of the transition metal and tin-containing peroxotitanic acid solution obtained at this time is from 1 to 9, with a pH of from 4 to 7 being preferred from the standpoint of safety during handling.

Step (2):

In Step (2), the transition metal and tin-containing peroxotitanic acid solution obtained in Step (1) is furnished to a hydrothermal reaction under pressure control and a temperature of from 80 to 250° C., preferably from 100 to 250° C., for 0.01 to 24 hours. From the standpoint of reaction efficiency and reaction controllability, a reaction temperature of from 80 to 250° C. is suitable. As a result, the transition metal and tin-containing peroxotitanic acid is converted to transition metal and tin-containing titanium oxide fine particles. Here, "under pressure control" means to carry out suitable pressurization in such a way as to be able to maintain the reaction temperature in cases where the reaction temperature exceeds the boiling point of the dispersion medium. This includes control at atmospheric pressure in cases where the temperature is at or below the boiling point of the dispersion medium. The pressure used here is generally from about 0.12 MPa to about 4.5 MPa, preferably from about 0.15 MPa to about 4.5 MPa, and more preferably from about 0.20 MPa to about 4.5 MPa. The reaction time is preferably from 1 minute to 24 hours. Step (2) thus provides a dispersion of the transition metal and tin-containing titanium oxide fine particles that serve as the first type of titanium oxide fine particle.

The particle size of the titanium oxide fine particles thus obtained is preferably in the range already mentioned above, although control of the particle size by adjusting the reaction conditions is possible. For example, the particle size can be made smaller by shortening the reaction time.

Step (3):

In Step (3), separate from above Steps (1) and (2), an iron group element-containing peroxotitanic acid solution is prepared by reacting a starting titanium compound, an iron group compound, a basic substance and hydrogen peroxide in an aqueous dispersion medium. Aside from using an iron group compound in place of the transition metal compound and the tin compound in Step (1), the reaction is carried out in exactly the same way.

That is, the starting materials, these being a starting titanium compound, an iron group compound, an aqueous dispersion medium, a basic substance and hydrogen peroxide, each of which has been described above, are used by being compounded in the foregoing manner, and then furnished to a reaction under the temperature and time conditions mentioned above. The amount of hydrogen peroxide added is preferably set to from 1.5 to 20 times the number of moles of the iron group constituent and titanium combined.

The resulting iron group element-containing peroxotitanic acid solution may include also an alkaline substance or an acidic substance in order to, for example, adjust the pH. The alkaline substance and acidic substance, and pH adjustment as well, may be handled in the same way as described above.

Step (4):

In Step (4), the iron group element-containing peroxotitanic acid solution obtained in Step (3) is furnished to a hydrothermal reaction under pressure control and a temperature of from 80 to 250° C., preferably from 100 to 250° C., for 0.01 to 24 hours. From the standpoint of reaction efficiency and reaction controllability, a reaction temperature of from 80 to 250° C. is suitable. As a result, the iron group element-containing peroxotitanic acid is converted to iron group element-containing titanium oxide fine particles. Here, "under pressure control" means to carry out suitable pressurization in such a way as to be able to maintain the reaction temperature in cases where the reaction temperature exceeds the boiling point of the dispersion medium. This includes control at atmospheric pressure in cases where the temperature is at or below the boiling point of the dispersion medium. The pressure used here is generally from about 0.12 MPa to about 4.5 MPa, preferably from about 0.15 MPa to about 4.5 MPa, and more preferably from about 0.20 MPa to about 4.5 MPa. The reaction time is preferably from 1 minute to 24 hours. Step (4) thus provides a dispersion of the iron group element-containing titanium oxide fine particles that serve as the second type of titanium oxide fine particle.

The particle size of the titanium oxide fine particles thus obtained is preferably in the range already mentioned above, although control of the particle size by adjusting the reaction conditions is possible. For example, the particle size can be made smaller by shortening the reaction time.

Step (5):

In Step (5), the first titanium oxide fine-particle dispersion obtained from Steps (1) and (2) and the second titanium oxide fine-particle dispersion obtained from Steps (3) and (4) are mixed together. The mixing method is not particularly limited, and may consist of agitation with an agitator or dispersion with an ultrasonic disperser. The temperature at the time of mixture is preferably from 20 to 100° C., and the mixing time is preferably from 1 minute to 3 hours. As for the mixing ratio, mixing should be carried out such that the weight ratio between the titanium oxide fine particles in the respective titanium oxide fine-particle dispersions becomes the weight ratio already described above.

The weight of the titanium oxide fine particles contained in the titanium oxide fine-particle dispersion can be calculated from the amount and concentration of the titanium oxide fine-particle dispersion. Using the following formula, the concentration can be calculated from the weight of the nonvolatile matter (titanium oxide fine particles) remaining when a portion of the titanium oxide fine-particle dispersion is sampled and heated at 105° C. for 3 hours to evaporate the solvent and the weight of the sampled titanium oxide fine-particle dispersion.

Concentration (%) of titanium oxide fine-particle dispersion=[Weight of nonvolatile matter(g)/Weight of titanium oxide fine-particle dispersion(g)]×100

As noted above, from the standpoint of the ease of forming a surface layer (photocatalytic thin film) of the required thickness, the total concentration of the first type of titanium oxide fine particle and the second type of titanium oxide fine particle in the visible light-responsive photocatalytic titanium oxide fine-particle dispersion thus produced is preferably from 0.01 to 20 wt %, and more preferably from 0.5 to 10 wt %. With regard to adjustment of the concentration, when the concentration is higher than the desired concentration, the concentration can be lowered by adding aqueous solvent to dilute the dispersion; when the concentration is lower than the desired concentration, the concentration can be increased by evaporating or filtering off some of the aqueous solvent. The concentration can be determined as described above.

In cases where the above-described film formability-increasing binder is added, such addition is preferably carried out to a visible light-responsive photocatalytic titanium oxide fine-particle dispersion whose concentration has been adjusted as described above such that the desired concentration is achieved following mixture of the aqueous binder solution to be added.

<Interior Material Having Surface Layer Containing Visible Light-Responsive Photocatalytic Titanium Oxide>

The visible light-responsive photocatalytic titanium oxide fine-particle dispersion can be used for the purpose of forming a photocatalytic thin film (surface layer) on the surface of the main body of an interior material. The interior material can have a variety of shapes depending on its purpose and intended application.

In this specification, "interior material" includes members which are installed indoors, as exemplified by indoor construction materials used in buildings, such as wall materials, wall paper, ceiling materials, flooring, tile, bricks, wooden boards, resin boards, metal plates, tatami mats and bathroom materials; interior materials used in vehicles, such as wall materials, ceiling materials, flooring, seats, handles and straps in automobiles, rail cars and the like; furnishings such as curtains, blinds, floor coverings, partition panels, glass, mirrors, films, desks, chairs, beds and cabinets; and household appliances such as air purifiers, air conditioners, refrigerators, washing machines, personal computers, printers, tablets, touch panels and telephones.

Here, the various types of interior materials may be composed of, for example, organic materials or inorganic materials.

Illustrative examples of organic materials include synthetic resin materials such as vinyl chloride resins (PVC), polyethylene (PE), polypropylene (PP), polycarbonates (PC), acrylic resins, polyacetals, fluoroplastics, silicone resins, ethylene-vinyl acetate copolymers (EVA), acrylonitrile-butadiene rubbers (NBR), polyethylene terephthalate (PET), polyethylene naphthalate (PEN), polyvinyl butyral (PVB), ethylene-vinyl alcohol copolymers (EVOH), polyimide resins, polyphenylene sulfides (PPS), polyetherimides (PEI), polyetheretherimides (PEEI), polyetheretherketones (PEEK), melamine resins, phenolic resins and acrylonitrile-butadiene-styrene (ABS) resins; natural materials such as natural rubbers; and semi-synthetic materials made of the above synthetic resin materials and natural materials. These materials may be rendered into products of a required shape and construction, such as films, sheets, textile materials, textile products and other moldings or laminates.

Examples of inorganic materials include nonmetallic inorganic materials and metallic inorganic materials.

Examples of nonmetallic inorganic materials include glass, ceramic, stone and gypsum. These may be rendered into products of various forms, such as tile, glass, mirrors, walls and decorative materials.

Examples of metallic inorganic materials include cast iron, steel, iron, ferrous alloys, stainless steel, aluminum, aluminum alloys, nickel, nickel alloys and diecast zinc. These may be plated with the above metallic inorganic materials or coated with the above organic materials, or may be platings applied to the surface of the above organic materials or nonmetallic inorganic materials.

The method of forming a surface layer (photocatalytic thin film) on the surface of various types of interior material bodies is exemplified by applying the visible light-responsive photocatalytic titanium oxide fine-particle dispersion, or a liquid coating obtained by the further addition of a binder, onto the surface of the interior material body using a method such as spray coating, flow coating, dip coating, spin coating, Meyer bar coating, reverse roll coating, gravure coating, knife coating, kiss coating, die coating or film transfer, and subsequently drying the applied dispersion or liquid coating.

The drying temperature following application may be variously selected according to the substrate to which application is carried out, but is preferably from 0 to 500° C., more preferably from 5 to 200° C., and even more preferably from 10 to 150° C. The reasons for this range are that, at below 0° C., the liquid may freeze and become impossible to use, and at above 500° C., the photocatalytic activity may decrease.

The drying time following application may be variously selected according to the method of application and the drying temperature, but is preferably from 10 seconds to 72 hours, and more preferably from 20 seconds to 48 hours. The reasons for this range are that, at less than 10 seconds, anchoring of the photocatalytic thin film to the member surface may be inadequate, and at more than three days, the cost-effectiveness worsens, which is undesirable.

The thickness of the surface layer may be variously selected, but is preferably from 10 nm to 10 µm, more preferably from 20 nm to 5 µm, and even more preferably from 50 nm to 1 µm. The reasons for this range are that, at a layer thickness below 10 nm, the photocatalytic activity obtained may be inadequate, and at more than 10 µm, the surface layer may tend to peel from the surface of the interior material body.

The surface layer (photocatalytic thin film) formed in this way is transparent and not only provides, as in the prior art, good photocatalysis when exposed to light in the ultraviolet region (10 to 400 nm), but can also achieve excellent photocatalysis even, for example, indoors when exposed only to visible-spectrum light (400 to 800 nm) from which conventional photocatalysts have been unable to obtain sufficient photocatalysis. Owing to photocatalysis by titanium oxide, the interior material on which this surface layer has been formed decomposes organic matter adsorbed to the surface, thus making it possible to exhibit effects such as cleaning, deodorizing and disinfection of the interior material surface.

EXAMPLES

The invention is illustrated more fully below by way of Working Examples and Comparative Examples, although these Examples are not intended to limit the invention. The various measurements in the invention were carried out as described below.

(1) Average Particle Size ($D_{50}$) of Titanium Oxide Fine Particles in Dispersion The average particle size ($D_{50}$) of titanium oxide fine particles in a dispersion was measured using a particle size analyzer (trade name: "Nanotrac UPA-EX150"; from Nikkiso Co., Ltd.).

(2) Test of Photocatalytic Thin-Film Performance in Decomposition of Acetaldehyde Gas (Under LED Irradiation)

The photocatalytic activity of the interior material (photocatalytic thin film) of the invention formed by applying and drying the dispersion was evaluated by means of decomposition reactions on acetaldehyde gas, which is a volatile organic compound (VOC). Evaluation was carried out as follows by a batch-type method for evaluating gas decomposition performance.

An interior material fashioned to an A4 size (210 mm×297 mm) was set within a 5 L capacity stainless steel cell having a quartz glass window, following which the cell was filled with 5 ppm concentration acetaldehyde gas that was moisture-conditioned to 50% humidity, and the interior material was exposed to light at an illuminance of 30,000 Lx using an LED lamp (model number: TH-211×200SW, from CCS Inc.; spectral distribution, 400 to 800 nm) positioned at the top of the cell. When acetaldehyde gas decomposes on account of the photocatalyst applied to the interior material, the acetaldehyde gas concentration within the cell decreases. By measuring this concentration, the amount of acetaldehyde gas that has decomposed can be determined. The acetaldehyde gas concentration was measured with a photoacoustic multigas monitor (trade name: INNOVA 1412, from LumaSense Technologies Inc.), and evaluation was carried out based on the following criteria by comparing the time it took for the concentration of acetaldehyde gas to decrease to 1 ppm from the initial concentration of 5 ppm. The test was performed for up to 72 hours.

Excellent (⊚): Decreases to reference value in 24 hours or less

Good (○): Decreases to reference value in 72 hours or less

Marginal (Δ): A decrease from initial concentration (5 ppm) is observable, but cannot decrease to 1 ppm within 72 hours No Good (x): No decrease from initial concentration (5 ppm) is observable (no decrease whatsoever)

(3) Identification of Crystal Phases of Titanium Oxide Fine Particles

The crystal phases of the titanium oxide fine particles were identified by powder x-ray diffraction analysis (using a desktop x-ray powder diffractometer available under the trade name D2 PHASER from Bruker AXS) on the titanium oxide fine-particle powders recovered by drying the resulting titanium oxide fine-particle dispersions at 105° C. for 3 hours.

Working Example 1

<Preparation of Dispersion of Titanium Oxide Fine Particles Containing Tin and Molybdenum in Solid Solution>

A tin and molybdenum-containing titanium hydroxide precipitate was obtained by adding and dissolving tin(IV) chloride in a 36 wt % aqueous solution of titanium(IV) chloride to a Ti/Sn molar ratio of 20, diluting this ten-fold with pure water, and then gradually adding to this aqueous solution 10 wt % ammonia water in which molybdenum(VI) oxide had been added and dissolved to a Ti/Mo molar ratio of 20 based on the titanium constituent in the aqueous solution of titanium(IV) chloride, thereby effecting neutralization and hydrolysis. The pH of the solution at this time was 8. The resulting precipitate was deionization treated by the repeated addition of pure water and decantation. Next, 35 wt % hydrogen peroxide water was added to the deionization-treated tin and molybdenum-containing titanium hydroxide precipitate to a $H_2O_2/(Ti+Sn+Mo)$ molar ratio of 10, after which the system was stirred at 50° C. for three hours to fully carry out the reaction, thereby giving a clear, orange-colored tin and molybdenum-containing peroxotitanic acid solution (a).

A 500 mL autoclave was charged with 400 mL of the tin and molybdenum-containing peroxotitanic acid solution (a), and this was hydrothermally treated at 150° C. for 90 minutes. Next, the concentration was adjusted by adding pure water, thereby giving a dispersion (solids concentration, 1 wt %) of titanium oxide fine particles (A) containing tin and molybdenum in solid solution. Powder x-ray diffraction analysis was carried out on the titanium oxide fine particles (A), whereupon the only observed peaks were rutile-type titanium oxide peaks, indicating that the tin and molybdenum were in solid solution in the titanium oxide.

<Preparation of Dispersion of Titanium Oxide Fine Particles Containing Iron in Solid Solution>

An iron-containing titanium hydroxide precipitate was obtained by adding iron(III) chloride to a 36 wt % aqueous solution of titanium(IV) chloride to a Ti/Fe molar ratio of 10, diluting this ten-fold with pure water and then gradually adding to the aqueous solution 10 wt % ammonia water, thereby effecting neutralization and hydrolysis. The pH of the solution at this time was 8. The resulting precipitate was deionization treated by the repeated addition of pure water and decantation. Next, 35 wt % hydrogen peroxide water was added to the deionization-treated iron-containing titanium hydroxide precipitate to a $H_2O_2/(Ti+Fe)$ molar ratio of 8, after which the system was stirred at 40° C. for two hours to fully carry out the reaction, thereby giving a clear, orange-colored iron-containing peroxotitanic acid solution (b).

A 500 mL autoclave was charged with 400 mL of the iron-containing peroxotitanic acid solution (b), and this was hydrothermally treated at 130° C. for 90 minutes. Next, the concentration was adjusted by adding pure water, thereby giving a dispersion (solids concentration, 1 wt %) of titanium oxide fine particles (B) containing iron in solid solution. Powder x-ray diffraction analysis was carried out on the titanium oxide fine particles (B), whereupon the only observed peaks were anatase-type titanium oxide peaks, indicating that the iron was in solid solution in the titanium oxide.

A visible light-responsive photocatalytic titanium oxide fine-particle dispersion (e-1) was obtained by mixing together the respective dispersions of titanium oxide fine particles (A) and titanium oxide fine particles (B) such that the weight ratio of the titanium oxide fine particles (A) to the titanium oxide fine particles (B), expressed as (A):(B), becomes 50:50.

A liquid coating for evaluation (E-1) was produced by adding a silica-based binder (colloidal silica available under the trade name Snotex 20 from Nissan Chemical Industries, Ltd.; average particle size, 10 to 20 nm; an aqueous solution having a $SiO_2$ concentration of 20 wt %) to the photocatalytic titanium oxide fine-particle dispersion (e-1) so as to give a $TiO_2/SiO_2$ weight ratio of 1.5.

<Application onto Decorative Gypsum Board>

A decorative gypsum board for use as a ceiling panel was cut to an A4 size and the liquid coating for evaluation (E-1) was applied with an air spray gun (item model number "LPH-50-S9-10" from Anest Iwata Corporation) adjusted to a discharge pressure of 0.2 MPa such that the thickness of the photocatalytic fine particle-containing surface layer (photocatalytic thin film) becomes 80 nm, and then dried for 24 hours within a 20° C. chamber, giving a sample member for evaluation of the acetaldehyde gas decomposition performance. The acetaldehyde gas decomposition performance by this surface layer (photocatalytic thin film) was measured using the batch-type gas decomposition performance evaluation method, whereupon the acetaldehyde gas concentration decreased to 1 ppm after 15 hours of LED (wavelength, 400 to 800 nm) irradiation (Excellent: ⊚). The surface was visually examined under visible light from a distance of 20 cm, but no abnormalities were observed.

Application onto Melamine Veneer

Working Example 2

A melamine veneer for use as an indoor partition panel was cut to an A4 size and the liquid coating for evaluation (E-1) was applied with an air spray gun in the same way as in Working Example 1 such that the thickness of the photocatalytic fine particle-containing surface layer (photocatalytic thin film) becomes 60 nm, and then dried for 2 hours in an oven set to 50° C., giving a sample member for evaluation of the acetaldehyde gas decomposition performance. The acetaldehyde gas decomposition performance by this surface layer (photocatalytic thin film) was measured using the batch-type gas decomposition performance evaluation method, whereupon the acetaldehyde gas concentration decreased to 1 ppm after 40 hours of LED (wavelength, 400 to 800 nm) irradiation (Good: ○). The surface was visually examined under visible light from a distance of 20 cm, but no abnormalities were observed.

Application onto Floor Tile

Working Example 3

PVC floor tile used as indoor flooring was cut to an A4 size and the liquid coating for evaluation (E-1) was applied with an air spray gun in the same way as in Working Example 1 such that the thickness of the photocatalytic fine particle-containing surface layer (photocatalytic thin film) becomes 80 nm, and then dried for 1 hour in an oven set to 150° C., giving a sample member for evaluation of the acetaldehyde gas decomposition performance. The acetaldehyde gas decomposition performance by this surface layer (photocatalytic thin film) was measured using the batch-type gas decomposition performance evaluation method, whereupon the acetaldehyde gas concentration decreased to 1 ppm after 12 hours of LED (wavelength, 400 to 800 nm) irradiation (Excellent: ○). The surface was visually examined under visible light from a distance of 20 cm, but no abnormalities were observed.

Working Example 4

Application onto Indoor Film

Corona surface-treated PET film (model number "Lumirror T60" from Toray Industries, Inc.) was cut to an A4 size and the liquid coating for evaluation (E-1) prepared in Working Example 1 was applied with a bar coater to the corona surface-treated film surface such that the thickness of the photocatalytic fine particle-containing surface layer (photocatalytic thin film) becomes 100 nm, and then dried for 5 minutes in an oven set to 80° C., giving a sample member for evaluation of the acetaldehyde gas decomposition performance. The acetaldehyde gas decomposition performance by this surface layer (photocatalytic thin film) was measured using the batch-type gas decomposition performance evaluation method, whereupon the acetaldehyde gas concentration decreased to 1 ppm after 12 hours of LED (wavelength, 400 to 800 nm) irradiation (Excellent: ⊚). The surface was visually examined under visible light from a distance of 20 cm, but no abnormalities were observed.

Working Example 5

<Preparation of Dispersion of Titanium Oxide Fine Particles Containing Tin and Vanadium in Solid Solution>

A tin and vanadium-containing titanium hydroxide precipitate was obtained by adding and dissolving tin(IV) chloride and vanadyl(IV) sulfate in a 36 wt % aqueous solution of titanium(IV) chloride to a Ti/Sn molar ratio of 20 and a Ti/V molar ratio of 2,000, diluting this ten-fold with pure water, and then gradually adding to this aqueous solution 10 wt % ammonia water and effecting neutralization and hydrolysis, thereby giving a tin and vanadium-containing titanium hydroxide precipitate. The pH of the solution at this time was 8.5. The resulting precipitate was deionization treated by the repeated addition of pure water and decantation. Next, 35 wt % hydrogen peroxide water was added to the deionization-treated tin and vanadium-containing titanium hydroxide precipitate to a $H_2O_2/(Ti+Sn+V)$ molar ratio of 10, after which the system was stirred at 50° C. for three hours to fully carry out the reaction, thereby giving a clear, orange-colored tin and vanadium-containing peroxotitanic acid solution (c).

A 500 mL autoclave was charged with 400 mL of the tin and vanadium-containing peroxotitanic acid solution (c), and this was hydrothermally treated at 150° C. for 90 minutes. Next, the concentration was adjusted by adding pure water, thereby giving a dispersion (solids concentration, 1 wt %) of titanium oxide fine particles (C) containing tin and vanadium in solid solution. Powder x-ray diffraction analysis was carried out on the titanium oxide fine particles (C), whereupon the only observed peaks were rutile-type titanium oxide peaks, indicating that the tin and vanadium were in solid solution in the titanium oxide.

The visible light-responsive photocatalytic titanium oxide fine-particle dispersion (e-2) of this Working Example was obtained by mixing together the respective dispersions of titanium oxide fine particles (C) and titanium oxide fine particles (B) such that the weight ratio of the titanium oxide fine particles (C) to the titanium oxide fine particles (B), expressed as (C):(B), becomes 50:50.

A liquid coating for evaluation (E-2) was produced by adding a silica-based binder (colloidal silica available under the trade name Snotex 20 from Nissan Chemical Industries, Ltd.; average particle size, 10 to 20 nm; an aqueous solution having a $SiO_2$ concentration of 20 wt %) to the photocatalytic titanium oxide fine particle dispersion (e-2) so as to give a $TiO_2/SiO_2$ weight ratio of 1.5.

<Application onto Melamine Veneer>

A melamine veneer for use as an indoor partition panel was cut to an A4 size and the liquid coating for evaluation (E-2) was applied with an air spray gun in the same way as in Working Example 1 such that the thickness of the photocatalytic fine particle-containing surface layer (photocatalytic thin film) becomes 60 nm, and then dried for 2 hours in an oven set to 50° C., giving a sample member for evaluation of the acetaldehyde gas decomposition performance. The acetaldehyde gas decomposition performance by this surface layer (photocatalytic thin film) was measured using the batch-type gas decomposition performance evaluation method, whereupon the acetaldehyde gas concentration decreased to 1 ppm after 59 hours of LED (wavelength, 400 to 800 nm) irradiation (Good: O). The surface was visually examined under visible light from a distance of 20 cm, but no abnormalities were observed.

Working Example 6

<Preparation of Dispersion of Titanium Oxide Fine Particles Containing Tin and Molybdenum in Solid Solution>

A tin and molybdenum-containing titanium hydroxide precipitate was obtained by adding and dissolving tin(IV) chloride in a 36 wt % aqueous solution of titanium(IV) chloride to a Ti/Sn molar ratio of 5, diluting this ten-fold with pure water, and then gradually adding to this aqueous solution 10 wt % ammonia water in which molybdenum(VI) oxide had been added and dissolved to a Ti/Mo molar ratio of 50 based on the titanium constituent in the aqueous solution of titanium(IV) chloride, thereby effecting neutralization and hydrolysis. The pH of the solution at this time was 8. The resulting precipitate was deionization treated by the repeated addition of pure water and decantation. Next, 35 wt % hydrogen peroxide water was added to the deionization-treated tin and molybdenum-containing titanium hydroxide precipitate to a $H_2O_2/(Ti+Sn+Mo)$ molar ratio of 10, after which the system was stirred at 50° C. for three hours to fully carry out the reaction, thereby giving a clear, orange-colored tin and molybdenum-containing peroxotitanic acid solution (d).

A 500 mL autoclave was charged with 400 mL of the tin and molybdenum-containing peroxotitanic acid solution (d), and this was hydrothermally treated at 150° C. for 90 minutes. Next, the concentration was adjusted by adding pure water, thereby giving a dispersion (solids concentration, 1 wt %) of titanium oxide fine particles (D) containing tin and molybdenum in solid solution. Powder x-ray diffraction analysis was carried out on the titanium oxide fine particles (D), whereupon the only observed peaks were rutile-type titanium oxide peaks, indicating that the tin and molybdenum were in solid solution in the titanium oxide.

<Preparation of Dispersion of Titanium Oxide Fine Particles Containing Iron in Solid Solution>

An iron-containing titanium hydroxide precipitate was obtained by adding iron(III) chloride to a 36 wt % aqueous solution of titanium(IV) chloride to a Ti/Fe molar ratio of 100, diluting this ten-fold with pure water and then gradually adding to the aqueous solution 10 wt % ammonia water, thereby effecting neutralization and hydrolysis. The pH of the solution at this time was 8. The resulting precipitate was deionization treated by the repeated addition of pure water and decantation. Next, 35 wt % hydrogen peroxide water was added to the deionization-treated iron-containing titanium hydroxide precipitate to a $H_2O_2/(Ti+Fe)$ molar ratio of 8, after which the system was stirred at 40° C. for two hours to fully carry out the reaction, thereby giving a clear, orange-colored iron-containing peroxotitanic acid solution (e).

A 500 mL autoclave was charged with 400 mL of the iron-containing peroxotitanic acid solution (e), and this was hydrothermally treated at 130° C. for 90 minutes. Next, the concentration was adjusted by adding pure water, thereby giving a dispersion (solids concentration, 1 wt %) of titanium oxide fine particles (E) containing iron in solid solution. Powder x-ray diffraction analysis was carried out on the titanium oxide fine particles (E), whereupon the only observed peaks were anatase-type titanium oxide peaks, indicating that the iron was in solid solution in the titanium oxide.

A visible light-responsive photocatalytic titanium oxide fine-particle dispersion (e-3) was obtained by mixing together the respective dispersions of titanium oxide fine particles (D) and titanium oxide fine particles (E) such that the weight ratio of the titanium oxide fine particles (D) to the titanium oxide fine particles (E), expressed as (D):(E), becomes 70:30.

A liquid coating for evaluation (E-3) was produced by adding a silica-based binder (colloidal silica available under the trade name Snotex 20 from Nissan Chemical Industries, Ltd.; average particle size, 10 to 20 nm; an aqueous solution having a $SiO_2$ concentration of 20 wt %) to the photocatalytic titanium oxide fine-particle dispersion (e-3) so as to give a $TiO_2/SiO_2$ weight ratio of 3.

<Application onto Decorative Gypsum Board>

A decorative gypsum board for use as a ceiling panel was cut to an A4 size and the liquid coating for evaluation (E-3) was applied with an air spray gun (model number "LPH-50-S9-10" from Anest Iwata Corporation) adjusted to a discharge pressure of 0.2 MPa such that the thickness of the photocatalytic fine particle-containing surface layer (photocatalytic thin film) becomes 80 nm, and then dried for 24 hours within a 20° C. chamber, giving a sample member for evaluation of the acetaldehyde gas decomposition performance. The acetaldehyde gas decomposition performance by this surface layer (photocatalytic thin film) was measured using the batch-type gas decomposition performance evaluation method, whereupon the acetaldehyde gas concentration decreased to 1 ppm after 45 hours of LED (wavelength, 400 to 800 nm) irradiation (Good: O). The surface was visually examined under visible light from a distance of 20 cm, but no abnormalities were observed.

Working Example 7

<Preparation of Dispersion of Titanium Oxide Fine Particles Containing Tin and Molybdenum in Solid Solution>

A tin and molybdenum-containing titanium hydroxide precipitate was obtained by adding and dissolving tin(IV) chloride in a 36 wt % aqueous solution of titanium(IV) chloride to a Ti/Sn molar ratio of 100, diluting this ten-fold with pure water, and then gradually adding to this aqueous solution 10 wt % ammonia water in which molybdenum(VI) oxide had been added and dissolved to a Ti/Mo molar ratio of 5 based on the titanium constituent in the aqueous solution of titanium(IV) chloride, thereby effecting neutralization and hydrolysis. The pH of the solution at this time was 8. The resulting precipitate was deionization treated by the repeated addition of pure water and decantation. Next, 35 wt % hydrogen peroxide water was added to the deionization-treated tin and molybdenum-containing titanium hydroxide precipitate to a $H_2O_2/(Ti+Sn+Mo)$ molar ratio of 10, after which the system was stirred at 50° C. for three hours to fully carry out the reaction, thereby giving a clear, orange-colored tin and molybdenum-containing peroxotitanic acid solution (0.

A 500 mL autoclave was charged with 400 mL of the tin and molybdenum-containing peroxotitanic acid solution (0, and this was hydrothermally treated at 150° C. for 90 minutes. Next, the concentration was adjusted by adding pure water, thereby giving a dispersion (solids concentration, 1 wt %) of titanium oxide fine particles (F) containing tin and molybdenum in solid solution. Powder x-ray diffraction analysis was carried out on the titanium oxide fine particles (F), whereupon the only observed peaks were anatase-type titanium oxide and rutile-type titanium oxide peaks, indicating that the tin and molybdenum were in solid solution in the titanium oxide.

A visible light-responsive photocatalytic titanium oxide fine-particle dispersion (e-4) was obtained by mixing together the respective dispersions of titanium oxide fine particles (F) and titanium oxide fine particles (B) such that the weight ratio of the titanium oxide fine particles (F) to the titanium oxide fine particles (B), expressed as (F):(B), becomes 80:20.

A liquid coating for evaluation (E-4) was produced by adding a silica-based binder (colloidal silica available under the trade name Snotex 20 from Nissan Chemical Industries, Ltd.; average particle size, 10 to 20 nm; an aqueous solution having a $SiO_2$ concentration of 20 wt %) to the photocatalytic titanium oxide fine-particle dispersion (e-4) so as to give a $TiO_2/SiO_2$ weight ratio of 2.

<Application onto Melamine Veneer>

A melamine veneer for use as an indoor partition panel was cut to an A4 size and the liquid coating for evaluation (E-4) was applied with an air spray gun in the same way as in Working Example 1 such that the thickness of the photocatalytic fine particle-containing surface layer (photocatalytic thin film) becomes 60 nm, and then dried for 2 hours in an oven set to 50° C., giving a sample member for evaluation of the acetaldehyde gas decomposition performance. The acetaldehyde gas decomposition performance by this surface layer (photocatalytic thin film) was measured using the batch-type gas decomposition performance evaluation method, whereupon the acetaldehyde gas concentration decreased to 1 ppm after 70 hours of LED (wavelength, 400 to 800 nm) irradiation (Good: ○). The surface was visually examined under visible light from a distance of 20 cm, but no abnormalities were observed.

Working Example 8

<Preparation of Dispersion of Titanium Oxide Fine Particles Containing Tin, Vanadium and Molybdenum in Solid Solution>

A tin, vanadium and molybdenum-containing titanium hydroxide precipitate was obtained by adding and dissolving tin(IV) chloride and vanadyl(IV) sulfate in a 36 wt % aqueous solution of titanium(IV) chloride to a Ti/Sn molar ratio of 10 and a Ti/V molar ratio of 100, diluting this ten-fold with pure water, and then gradually adding to this aqueous solution 10 wt % ammonia water in which molybdenum(VI) oxide had been added and dissolved to a Ti/Mo molar ratio of 500 based on the titanium constituent in the aqueous solution of titanium(IV) chloride, thereby effecting neutralization and hydrolysis. The pH of the solution at this time was 8.5. The resulting precipitate was deionization treated by the repeated addition of pure water and decantation. Next, 35 wt % hydrogen peroxide water was added to the deionization-treated tin and vanadium-containing titanium hydroxide precipitate to a $H_2O_2/(Ti+Sn+V+Mo)$ molar ratio of 10, after which the system was stirred at 50° C. for three hours to fully carry out the reaction, thereby giving a clear, orange-colored tin, vanadium and molybdenum-containing peroxotitanic acid solution (g).

A 500 mL autoclave was charged with 400 mL of the tin and vanadium-containing peroxotitanic acid solution (g), and this was hydrothermally treated at 150° C. for 90 minutes. Next, the concentration was adjusted by adding pure water, thereby giving a dispersion (solids concentration, 1 wt %) of titanium oxide fine particles (G) containing tin and vanadium in solid solution. Powder x-ray diffraction analysis was carried out on the titanium oxide fine particles (G), whereupon the only observed peaks were rutile-type titanium oxide peaks, indicating that the tin and vanadium were in solid solution in the titanium oxide.

A visible light-responsive photocatalytic titanium oxide fine-particle dispersion (e-5) was obtained by mixing together the respective dispersions of titanium oxide fine particles (G) and titanium oxide fine particles (B) such that the weight ratio of the titanium oxide fine particles (G) to the titanium oxide fine particles (B), expressed as (G):(B), becomes 60:40.

A liquid coating for evaluation (E-5) was produced by adding a silica-based binder (colloidal silica available under the trade name Snotex 20 from Nissan Chemical Industries, Ltd.; average particle size, 10 to 20 nm; an aqueous solution having a $SiO_2$ concentration of 20 wt %) to the photocatalytic titanium oxide fine-particle dispersion (e-5) so as to give a $TiO_2/SiO_2$ weight ratio of 2.

<Application onto Floor Tile>

PVC floor tile used as indoor flooring was cut to an A4 size and the liquid coating for evaluation (E-5) was applied with an air spray gun in the same way as in Working Example 1 such that the thickness of the photocatalytic fine particle-containing surface layer (photocatalytic thin film) becomes 80 nm, and then dried for 1 hour in an oven set to 150° C., giving a sample member for evaluation of the acetaldehyde gas decomposition performance. The acetaldehyde gas decomposition performance by this surface layer (photocatalytic thin film) was measured using the batch-type gas decomposition performance evaluation method, whereupon the acetaldehyde gas concentration decreased to 1 ppm after 65 hours of LED (wavelength, 400 to 800 nm) irradiation (Good: 0). The surface was visually examined under visible light from a distance of 20 cm, but no abnormalities were observed.

COMPARATIVE EXAMPLE 1

<Preparation of Titanium Oxide Fine-Particle Dispersion>

A titanium hydroxide precipitate was obtained by diluting a 36 wt % aqueous solution of titanium(IV) chloride ten-fold with pure water and then gradually adding 10 wt % ammonia water, thereby effecting neutralization and hydrolysis. The pH of the solution at this time was 9. The resulting precipitate was deionization treated by the repeated addition of pure water and decantation. Following deionization treatment, 35 wt % hydrogen peroxide water was added to the titanium hydroxide precipitate to a $H_2O_2/Ti$ molar ratio of 5, after which the system was stirred at room temperature for a full day and night to fully effect the reaction, thereby giving a clear, orange-colored peroxotitanic acid solution (h).

A 500 mL autoclave was charged with 400 mL of the peroxotitanic acid solution (h), and this was hydrothermally treated at 130° C. for 90 minutes. Next, the concentration was adjusted by adding pure water, thereby giving a dispersion (solids concentration, 1 wt %) of titanium oxide fine particles (H). Powder x-ray diffraction analysis was carried out on the titanium oxide fine particles (H), whereupon the observed peaks were anatase-type titanium oxide peaks.

A titanium oxide fine-particle dispersion (c-1) was obtained from a dispersion of titanium oxide fine particles (H) alone.

A liquid coating for evaluation (C-1) was obtained by, in the same way as in Working Example 1, adding a silica-based binder (colloidal silica available under the trade name Snotex 20 from Nissan Chemical Industries, Ltd.; average particle size, 10 to 20 nm; an aqueous solution having a $SiO_2$ concentration of 20 wt %) to the titanium oxide fine-particle dispersion (c-1) so as to give a TiO$_2$/SiO$_2$ weight ratio of 1.5.
<Application onto Decorative Gypsum Board>

Aside from using liquid coating for evaluation (C-1), a sample for evaluation of the acetaldehyde gas decomposition performance was produced in the same way as in Working Example 1. The acetaldehyde gas decomposition performance was measured, whereupon a decrease in the acetaldehyde gas concentration was not observed even after 72 hours of LED irradiation (No Good: x).

Comparative Example 2

A titanium oxide fine-particle dispersion (c-2) was obtained from a dispersion of titanium oxide fine particles (A) alone.

A liquid coating for evaluation (C-2) was obtained by, in the same way as in Working Example 1, adding a silica-based binder (colloidal silica available under the trade name Snotex 20 from Nissan Chemical Industries, Ltd.; average particle size, 10 to 20 nm; an aqueous solution having a SiO$_2$ concentration of 20 wt %) to the titanium oxide fine-particle dispersion (c-2) so as to give a TiO$_2$/SiO$_2$ weight ratio of 1.5.
<Application onto Melamine Veneer>

Aside from using liquid coating for evaluation (C-2), a sample for evaluation of the acetaldehyde gas decomposition performance was produced in the same way as in Working Example 2. The acetaldehyde gas decomposition performance was measured, whereupon the acetaldehyde gas concentration did not fall below 1 ppm even after 72 hours of LED irradiation (Marginal: Δ).

Comparative Example 3

A titanium oxide fine-particle dispersion (c-3) was obtained using a dispersion of titanium oxide fine particles (B) alone.

A liquid coating for evaluation (C-3) was obtained by, in the same way as in Working Example 1, adding a silica-based binder (colloidal silica available under the trade name Snotex 20 from Nissan Chemical Industries, Ltd.; average particle size, 10 to 20 nm; an aqueous solution having a SiO$_2$ concentration of 20 wt %) to the titanium oxide fine-particle dispersion (c-3) so as to give a TiO$_2$/SiO$_2$ weight ratio of 1.5.
<Application onto Floor Tile>

Aside from using liquid coating for evaluation (C-3), a sample for evaluation of the acetaldehyde gas decomposition performance was produced in the same way as in Working Example 3. The acetaldehyde gas decomposition performance was measured, whereupon a decrease in the acetaldehyde gas concentration was not observed even after 72 hours of LED irradiation (No Good: x).

As is apparent from the results of Working Examples 1 to 8, interior materials having a surface layer that includes a photocatalyst composed of, in admixture, a first type of titanium oxide fine particle containing in solid solution a tin constituent and a visible light responsiveness-increasing transition metal constituent (a molybdenum constituent and/or a vanadium constituent) and a second type of titanium oxide fine particle containing in solid solution an iron constituent can decompose acetaldehyde gas even under irradiation with LEDs that emit only visible-spectrum light.

As is apparent from the results in Comparative Example 1, in an interior material having a surface layer that includes a photocatalyst composed of ordinary titanium oxide fine particles, a sufficient photocatalytic activity is not obtained under visible light irradiation.

As is apparent from Comparative Examples 2 and 3, a sufficient photocatalytic activity cannot be obtained under visible light irradiation with only the first type of titanium oxide fine particle or with only the second type of titanium oxide fine particle.

Evaluation results for Working Examples 1 to 8 and Comparative Examples 1 to 3 are presented in Table 1.

TABLE 1

|  |  | Type of interior material | Liquid coating for evaluation | Average particle size (nm) | Time to 1 ppm (hours) | Rating |
|---|---|---|---|---|---|---|
| Working Example | 1 | decorative gypsum board | E-1 | 15 | 15 | ◎ |
|  | 2 | melamine veneer | E-1 | 15 | 40 | ○ |
|  | 3 | floor tiles | E-1 | 15 | 12 | ◎ |
|  | 4 | indoor film | E-1 | 15 | 12 | ◎ |
|  | 5 | melamine veneer | E-2 | 16 | 59 | ○ |
|  | 6 | decorative gypsum board | E-3 | 18 | 45 | ○ |
|  | 7 | melamine veneer | E-4 | 13 | 70 | ○ |
|  | 8 | floor tiles | E-5 | 12 | 65 | ○ |
| Comparative Example | 1 | decorative gypsum board | C-1 | 20 | no decomposition | X |
|  | 2 | melamine veneer | C-2 | 12 | 3.9 ppm after 72 hours | Δ |
|  | 3 | floor tiles | C-3 | 18 | no decomposition | X |

The invention claimed is:

1. An interior material comprising:
a surface layer having a visible light-responsive catalytic activity which decomposes organic matter adsorbed to the surface layer, wherein the surface layer comprises two types of titanium oxide fine particles: a first type of titanium oxide fine particle which contains in solid solution a tin constituent and a transition metal constituent (exclusive of iron group constituents) that increases visible light responsiveness, and a second type of titanium oxide fine particle which contains in solid solution an iron group constituent,
the transition metal constituent in solid solution within the first type of titanium oxide fine particle is at least one selected from the group consisting of molybdenum and vanadium, and
the first type of titanium oxide fine particle and the second type of titanium oxide fine particle have a mixing ratio therebetween, expressed as a weight ratio [(first type of titanium oxide fine particle)/(second type of titanium oxide fine particle)], of from 9 to 1, and wherein the interior material is a member selected from the group consisting of indoor construction materials, interior materials within a vehicle, furnishings and electrical appliances, and a crystal phase of the first type of titanium oxide fine particle is chiefly rutile and a crystal phase of the second type of titanium oxide fine particle is chiefly anatase.

2. The interior material of claim 1, wherein the content of the tin constituent included in the first type of titanium oxide fine particle, expressed as a molar ratio with titanium (Ti/Sn), is from 1 to 1,000.

3. The interior material of claim 1, wherein the content of the molybdenum constituent included in the first type of titanium oxide fine particle, expressed as a molar ratio with titanium (Ti/Mo), is from 1 to 1,000 and/or the content of the vanadium constituent, expressed as a molar ratio with titanium (Ti/V), is from 10 to 10,000.

4. The interior material of claim 1, wherein the content of the iron group constituent included in the second type of titanium oxide fine particle, expressed as a molar ratio with titanium (Ti/iron group constituent), is from 1 to 1,000.

5. The interior material of claim 1, wherein the iron group constituent in solid solution within the second type of titanium oxide fine particle is an iron constituent.

6. The interior material of claim 1, wherein the surface layer further comprises a binder.

7. The interior material of claim 6, wherein the binder is a silicon compound-based binder.

8. The interior material of claim 1, wherein the transition metal constituent in solid solution within the first type of titanium oxide fine particle is molybdenum.

9. The interior material of claim 1, wherein the transition metal constituent in solid solution within the first type of titanium oxide fine particle is vanadium.

10. The interior material of claim 1, wherein the transition metal constituent in solid solution within the first type of titanium oxide fine particle is molybdenum and vanadium.

11. The interior material of claim 1, wherein the first type of titanium oxide fine particle and the second type of titanium oxide fine particle have the mixing ratio therebetween, expressed as a weight ratio [(first type of titanium oxide fine particle)/(second type of titanium oxide fine particle)], of approximately 1.

12. The interior material of claim 1, wherein the second type of titanium oxide fine particle consists of titanium oxide and an iron group constituent in solid solution.

13. The interior material of claim 1, wherein the interior material is composed of an organic material or inorganic material selected from the group consisting of vinyl chloride resin (PVC), polyethylene terephthalate (PET), melamine resin and gypsum.

14. The interior material of claim 1, wherein the thickness of the surface layer is from 10 nm to 10 µm.

15. The interior material of claim 1, wherein said surface layer cleans, deodorizes and/or disinfects said interior material by decomposing said organic matter that adsorbed to the surface layer.

16. A method for decomposing organic matter on a surface of an interior material, comprising:
placing the interior material of claim 1 in an interior space and allowing the interior material to clean, deodorize and/or disinfect the interior material by decomposing organic matter that adsorbs to the interior material.

17. A method for producing an interior material, comprising the step of forming a surface layer having a visible light-responsive catalytic activity which decomposes organic matter adsorbed to the surface layer by applying, to the surface of an interior material body, a dispersion in which are dispersed two types of titanium oxide fine particles: a first type of titanium oxide fine particle which contains in solid solution a tin constituent and a transition metal constituent (exclusive of iron group constituents) that increases visible light responsiveness, and a second type of titanium oxide fine particle which contains in solid solution an iron group constituent, wherein the transition metal constituent in solid solution within the first type of titanium oxide fine particle is at least one selected from the group consisting of molybdenum and vanadium, and the first type of titanium oxide fine particle and the second type of titanium oxide fine particle have a mixing ratio therebetween, expressed as a weight ratio [(first type of titanium oxide fine particle)/(second type of titanium oxide fine particle)], of from 9 to 1, and wherein the interior material is a member selected from the group consisting of indoor construction materials, interior materials within a vehicle, furnishings and electrical appliances, and a crystal phase of the first type of titanium oxide fine particle is chiefly rutile and a crystal phase of the second type of titanium oxide fine particle is chiefly anatase.

18. The method for producing an interior material of claim 17, wherein the method of applying the dispersion is spray coating, flow coating, dip coating, spin coating, Meyer bar coating, gravure coating, knife coating, kiss coating, die coating or film transfer.

19. The method for producing an interior material of claim 17, wherein the transition metal constituent in solid solution within the first type of titanium oxide fine particle is molybdenum.

20. The method for producing an interior material of claim 17, wherein the transition metal constituent in solid solution within the first type of titanium oxide fine particle is vanadium.

21. The method for producing an interior material of claim 17, wherein the transition metal constituent in solid solution within the first type of titanium oxide fine particle is molybdenum and vanadium.

22. The method for producing an interior material of claim 17, wherein the first type of titanium oxide fine particle and the second type of titanium oxide fine particle have the mixing ratio therebetween, expressed as a weight ratio [(first type of titanium oxide fine particle)/(second type of titanium oxide fine particle)], of approximately 1.

* * * * *